(12) United States Patent
Sutherland et al.

(10) Patent No.: US 9,420,944 B2
(45) Date of Patent: Aug. 23, 2016

(54) METHOD OF PERFORMING A MINIMALLY-INVASIVE INTERVENTION

(71) Applicant: CardioPrecision Limited, Glasgow (GB)

(72) Inventors: Ying Sutherland, Glasgow (GB); Fraser William Havern Sutherland, Glasgow (GB)

(73) Assignee: CardioPrecision Limited, Glasgow (GB)

( * ) Notice: Subject to any disclaimer, the term of this patent is extended or adjusted under 35 U.S.C. 154(b) by 0 days.

(21) Appl. No.: 13/826,750

(22) Filed: Mar. 14, 2013

(65) Prior Publication Data

US 2013/0267785 A1     Oct. 10, 2013

Related U.S. Application Data

(63) Continuation of application No. 12/863,091, filed as application No. PCT/GB2009/000097 on Jan. 15, 2009.

(30) Foreign Application Priority Data

Jan. 17, 2008  (GB) .................................. 0800835.1

(51) Int. Cl.
  *A61B 1/32*   (2006.01)
  *A61B 17/02*  (2006.01)
  *A61B 17/00*  (2006.01)

(52) U.S. Cl.
  CPC ............. *A61B 1/32* (2013.01); *A61B 17/0218* (2013.01); *A61B 90/30* (2016.02); *A61B 90/36* (2016.02);

(Continued)

(58) Field of Classification Search
  CPC .............. A61B 17/02; A61B 17/0237; A61B 17/0243; A61B 19/5202
  USPC ......................................... 600/201, 245, 246
  See application file for complete search history.

(56) References Cited

U.S. PATENT DOCUMENTS 4,091,612 A    5/1978  Meisner et al.
D248,870 S     8/1978  Hass (Continued)

FOREIGN PATENT DOCUMENTS

DE        19629304 A1     1/1998
DE     202004001136 U1    4/2004

(Continued)

OTHER PUBLICATIONS

Jakober, F., "International Search Report" for PCT/GB2011/051618, as mailed Dec. 20, 2011, 3 pages.

(Continued)

*Primary Examiner* — Nicholas Plionis
(74) *Attorney, Agent, or Firm* — Winstead PC

(57) ABSTRACT

Apparatus for use in an operating theater equipped with a surgical table, comprises a lifting frame attachable to the surgical table and adapted for lifting a body part of a subject undergoing a surgical procedure upon the surgical table, and comprising an upright support post incorporating a jack, and a lifting arm pivotally mounted upon the post, whereby the arm can be turned about the upright support post on thrust bearing to either overhang the surgical table, or be pivoted away to permit access to the surgical table. The arm is adapted to support a retractor that comprises a blade portion incorporating a plurality of independent lighting devices positioned in light ports and configured to provide discrete illumination selectively to zones within the surgical field according to (a) a predetermined sequence program, or (b) a sequence determined by a user of the retractor.

22 Claims, 9 Drawing Sheets

(52) U.S. Cl.
CPC ............ *A61B 90/361* (2016.02); *A61B 90/50* (2016.02); *A61B 17/0281* (2013.01); *A61B 2017/00017* (2013.01); *A61B 2017/0237* (2013.01); *A61B 2090/306* (2016.02); *A61B 2090/309* (2016.02); *A61B 2090/372* (2016.02)

(56) References Cited

U.S. PATENT DOCUMENTS

| | | | |
|---|---|---|---|
| 4,562,832 A | 1/1986 | Wilder et al. | |
| 4,616,633 A | 10/1986 | Vargas Garcia | |
| 4,702,230 A | 10/1987 | Pelta | |
| 5,200,939 A | 4/1993 | Nishiwaki et al. | |
| 5,634,883 A | 6/1997 | Chin et al. | |
| 5,676,636 A | 10/1997 | Chin | |
| 5,941,819 A * | 8/1999 | Chin .......................... | 600/204 |
| 5,967,971 A | 10/1999 | Bolser | |
| 6,015,378 A | 1/2000 | Borst et al. | |
| 6,106,497 A * | 8/2000 | Wang ........................ | 604/122 |
| D433,134 S | 10/2000 | Pitesky | |
| 6,159,231 A * | 12/2000 | Looney et al. ............. | 606/206 |
| 6,274,859 B1 | 8/2001 | Yoshino et al. | |
| 6,347,168 B1 | 2/2002 | Shimomura et al. | |
| 6,355,030 B1 * | 3/2002 | Aldrich et al. ................. | 606/28 |
| 6,522,794 B1 | 2/2003 | Bischel et al. | |
| 6,965,710 B2 | 11/2005 | Makio | |
| D522,140 S | 5/2006 | Stalcup et al. | |
| D523,142 S | 6/2006 | Stalcup et al. | |
| 7,194,153 B1 | 3/2007 | Yajima et al. | |
| D568,471 S | 5/2008 | Engler | |
| D586,914 S | 2/2009 | DaSilva | |
| D589,145 S | 3/2009 | Miller | |
| D658,286 S | 4/2012 | Ryshkus et al. | |
| D669,171 S | 10/2012 | Boedeker | |
| 2001/0009971 A1 | 7/2001 | Sherts et al. | |
| 2003/0053744 A1 | 3/2003 | Makio | |
| 2003/0060686 A1 | 3/2003 | Taylor et al. | |
| 2003/0095781 A1 | 5/2003 | Williams | |
| 2004/0138685 A1* | 7/2004 | Clague .................. | A61B 17/12 606/167 |
| 2004/0242968 A1* | 12/2004 | Hill et al. ..................... | 600/210 |
| 2004/0260366 A1 | 12/2004 | Svanberg et al. | |
| 2005/0041909 A1 | 2/2005 | Nakano et al. | |
| 2005/0092333 A1* | 5/2005 | Cosgrove ...................... | 128/898 |
| 2005/0119530 A1* | 6/2005 | Douglas et al. ............. | 600/212 |
| 2005/0159650 A1 | 7/2005 | Raymond et al. | |
| 2006/0217596 A1 | 9/2006 | Williams | |
| 2006/0217597 A1 | 9/2006 | Vayser et al. | |
| 2007/0112256 A1 | 5/2007 | Terakawa et al. | |
| 2007/0129608 A1* | 6/2007 | Sandhu ........................ | 600/219 |
| 2007/0238932 A1 | 10/2007 | Jones et al. | |
| 2007/0263173 A1 | 11/2007 | Reimer et al. | |
| 2008/0002426 A1 | 1/2008 | Vayser et al. | |
| 2008/0113312 A1* | 5/2008 | Ortega ............................ | 433/29 |
| 2009/0244905 A1 | 10/2009 | Ishida et al. | |
| 2012/0154912 A1 | 6/2012 | Shihoh | |
| 2013/0155723 A1 | 6/2013 | Coleman | |
| 2014/0128141 A1 | 5/2014 | Bontempo et al. | |

FOREIGN PATENT DOCUMENTS

| | | |
|---|---|---|
| EP | 0101781 A1 | 3/1984 |
| EP | 0856286 A1 | 8/1998 |
| EP | 0993579 A1 | 4/2000 |
| EP | 1690498 A2 | 8/2006 |
| GB | 2133694 A | 8/1984 |
| JP | H01159615 A | 6/1989 |
| JP | H04268528 A | 9/1992 |
| JP | H04277423 A | 10/1992 |
| JP | H05273476 A | 10/1993 |
| JP | 07-136173 | 5/1995 |
| JP | 08-071073 | 3/1996 |
| JP | H10108824 A | 4/1998 |
| JP | 10277043 A | 10/1998 |
| JP | 3056375 U | 2/1999 |
| JP | 11-511366 | 10/1999 |
| JP | 2000007291 A | 1/2000 |
| JP | 2000166930 A | 6/2000 |
| JP | 2001042401 A | 2/2001 |
| JP | 2006156138 A | 6/2006 |
| SU | 1482675 A1 | 5/1989 |
| WO | WO-97/10753 A1 | 3/1997 |
| WO | WO-9923935 A1 | 5/1999 |
| WO | WO-0015116 A1 | 3/2000 |
| WO | WO-03/017847 A1 | 3/2003 |
| WO | WO-2004/044632 A1 | 5/2004 |
| WO | WO-2007084641 A2 | 7/2007 |
| WO | WO-2009/090383 A2 | 7/2009 |
| WO | WO-2012/038714 A1 | 3/2012 |

OTHER PUBLICATIONS

Sutherland, et al., U.S. Appl. No. 13/825,235, filed Aug. 30, 2011.
Sutherland, et al., U.S. Appl. No. 29/439,486, filed Dec. 11, 2012.
Lamelas, Joseph Intercostal Retractor System, "Miami Method Tailor-Made Exposure Products," Next Generation MICS Instrumentation, 2013, 5 pages.
Cosgrove III, Delos M., et al., "Minimally Invasive Approach for Aortic Valve Operations," The Society of Thoracic Surgeons, 1996, 2 pages.
Gundry, Steven R., et al., "Facile Minimally Invasive Cardiac Surgery via Ministernotomy," presented at Thirty-Third Annual Meeting of the Society of Thoracic Surgeons, Feb. 3-5, 1997, 5 pages.
Plass, Andre, et al., "Aortic Valve Replacement Through a Minimally Invasive Approach: Preoperative Planning, Surgical Technique, and Outcome," The Society of Thoracic Surgeons, 2009, 6 pages.
Murtuza, Bari, et al., "Minimal Access Aortic Valve Replacement: Is It Worth It?," The Society of Thoracic Surgeons, 2008, 11 pages.
Aesculap, "Valve XS: Instruments for Minimally Invasive Valve Surgery," Aesculap Surgical Technologies—Surgical Instruments, 2010, 27 pages.
Angeli, Markus, "International Search Report", for PCT/GB2009/000097 as mailed Sep. 18, 2009, 6 pages.
Ohtsuka, Toshiya, "Sternum lifting technique for thoracoscopic internal thoracic artery harvest", European Journal of Cardio-Thoracic Surgery, 2005, (5 pages).
Abdel-Wahab, Mohamed, et al.; "Update on Transcatheter Aortic Valve Replacement"; Trends in Cardiovascular Medicine, vol. 25, Issue 2; Feb. 2015; pp. 154-161.
Ampollini, Luca, et al.; "Transcervical Video-Assisted Thymectomy: Preliminary Results of a Modified Surgical Approach"; Langenbeck's Archive of Surgery, vol. 396, Issue 2; Dec. 30, 2010; pp. 267-271.
Babaliaros, Vasilis, et al.; "Comparison of Transfemoral Transcatheter Aortic Valve Replacement Performed in the Catheterization Laboratory (Minimalist Approach) versus Hybrid Operating Room (Standard Approach)"; JACC: Cardiovascular Interventions, vol. 7, No. 8; Aug. 2014; pp. 898-904.
Biancari, Fausto, et al.; "Immediate Outcome after Sutureless versus Transcatheter Aortic Valve Replacement"; Heart Vessels; Jan. 9, 2015; pp. 1-7.
Bramis, J., et al.; "Video-Assisted Transcervical Thymectomy"; Surg Endosc, vol. 18; Aug. 26, 2004; pp. 1535-1538.
Brown, Morgan L., et al.; "Ministernotomy versus Conventional Sternotomy for Aortic Valve Replacement: A Systematic Review and Meta-Analysis"; J Thorac Cardiovasc Surg, vol. 137, No. 3; Mar. 2009; pp. 670-679.
Byrne, John G., et al.; "Minimally Invasive Direct Access Heart Valve Surgery"; J Card Surg, vol. 15, No. 1; Jan. 2000; pp. 21-34.
Calhoun, Royce F., et al.; "Results of Transcervical Thymectomy for Myasthenia Gravis in 100 Consecutive Patients"; Annals of Surgery, vol. 230, No. 4; Apr. 15, 1999; pp. 555-561.
Clavel, Marie-Annick, et al.; "Validation and Characterization of Transcatheter Aortic Valve Effective Orifice Area Measured by Doppler Echocardiography"; JACC: Cardiovascular Imaging, vol. 4, No. 10; Oct. 2011; pp. 1053-1062.

(56) References Cited

OTHER PUBLICATIONS

Cooper, J.D., et al.; "An Improved Technique to Facilitate Transcervical Thymectomy for Myasthenia Gravis"; Ann Thorac Surg, vol. 45; Sep. 21, 1987; pp. 242-247.
Cosgrove, Delos M., et al.; "Minimally Invasive Approach for Aortic Valve Operations"; Ann Thorac Surg, vol. 62; Apr. 1996; pp. 596-597.
Czesla, Markus, et al.; "Safeguards and Pitfalls in Minimally Invasive Mitral Valve Surgery"; Ann Cardiothorac Surg, vol. 2, No. 6; Nov. 2013; pp. 849-852.
De Perrot, Marc, et al.; "Impact of Minimally Invasive Trans-Cervical Thymectomy on Outcome in Patients with Myasthenia Gravis"; Eur J Cardiothorac Surg, vol. 24, No. 5; Nov. 2003; pp. 677-683.
Deeb, Maher E., et al.; "Expanded Indications for Transcervical Thymectomy in the Management of Anterior Mediastinal Masses"; Ann Thorac Surg, vol. 72, No. 1; Jul. 2001; pp. 208-211.
Doss, M., et al.; "Sutureless Aortic Valve Replacement: Catheter-Based Transapical versus Direct Transaortic Implantation"; J Heart Valve Dis, vol. 21, No. 6; Nov. 2012; pp. 758-763 (abstract only, 2 pages).
Drews, Thorsten, et al.; "Elective Femoro-Femoral Cardiopulmonary Bypass during Transcatheter Aortic Valve Implantation: A Useful Tool"; J Thorac Cardiovasc Surg, vol. 145, No. 3; Mar. 12, 2012; pp. 757-763.
Ewe, See Hooi, et al.; "Location and Severity of Aortic Valve Calcium and Implications for Aortic Regurgitation after Transcatheter Aortic Valve Implantation"; Am J Cardiol, vol. 108, No. 10; Aug. 17, 2011; pp. 1470-1477.
Généreux, Philippe, et al.; "Paravalvular Leak after Transcatheter Aortic Valve Replacement"; J Am Coll Cardiol, vol. 61, No. 11; Mar. 19, 2013; pp. 1125-1136.
Glauber, Mattia, et al.; "Minimally Invasive Aortic Valve Surgery: State of the Art and Future Directions"; Ann Cardiothorac Surg, vol. 4, No. 1; Jan. 2015; pp. 26-32.
Glauber, Mattia, et al.; "Minimally Invasive Aortic Valve Replacement via Right Anterior Minithoracotomy: Early Outcomes and Midterm Follow-Up"; J Thorac Cardiovasc Surg, vol. 142, No. 6; Jul. 4, 2011; pp. 1577-1579.
Gopaldas, RR, et al.; "Why Choose Cardiothoracic Surgery as a Career?"; Heart Surg Forum, vol. 14, No. 3; Jun. 2011; pp. E142-E148 (abstract only, 2 pages).
Grossi, Eugene A., et al.; "Comparison of Post-Operative Pain, Stress Response, and Quality of Life in Port Access vs. Standard Sternotomy Coronary Bypass Patients"; Eur J Cardiothorac Surg, vol. 16 (Suppl. 2); Nov. 1999; S39-S42.
Gundry, Steven R., et al.; "Facile Minimally Invasive Cardiac Surgery via Ministernotomy"; Ann Thorac Surg, vol. 65, No. 4; Feb. 3, 1997; pp. 1100-1104.
Healy, Samuel E., et al.; "Thiel Embalming Method for Cadaver Preservation: A Review of New Training Model for Urologic Skills Training"; Urology, vol. 85, Issue. 3; Mar. 2015; pp. 499-504.
Huang, CS, et al.; "Factors Influencing the Outcome of Transsternal Thymectomy for Myasthenia Gravis"; Acta Neurol Scand, vol. 112, Issue 2; May 26, 2005; pp. 108-114.
Kappetein, A. Pieter, et al.; "Updated Standardized Endpoint Definitions for Transcatheter Aortic Valve Implantation: The Valve Academic Research Consortium-2 Consensus Document"; J Thorac Cardiovasc Surg, vol. 145, No. 1; Oct. 16, 2012; pp. 6-23.
Kas, József, et al.; "Decade-Long Experience with Surgical Therapy of Myasthenia Gravis: Early Complications of 324 Transsternal Thymectomies"; Ann Thorac Surg, vol. 72, Issue 5; Nov. 2001; pp. 1691-1697.

Khoshbin, E., et al.; "Mini-Sternotomy for Aortic Valve Replacement reduces the Length of Stay in the Cardiac Intensive Care Unit: Meta-Analysis of Randomised Controlled Trials"; BMJ Open, vol. 1, No. 2; Nov. 24, 2011; pp. 1-5.
Kiser, Andy C., et al.; "Suprasternal Direct Aortic Approach Transcatheter Aortic Valve Replacement Avoids Sternotomy and Thoracotomy: First-in-Man Experience"; Eur J Cardiothorac Surg, vol. 48, Issue 5; Oct. 2014; 7 pages.
Leon, Martin B., et al.; "Standardized Endpoint Definitions for Transcatheter Aortic Valve Implantation Clinical Trials: A Consensus Report from the Valve Academic Research Consortium"; Eur Heart J, vol. 32, No. 2; Jan. 6, 2011; pp. 205-217.
Mangner, Norman, et al.; "Remaining Pitfalls and Limitations of TAVI in 2014"; EuroIntervention, vol. 10; Sep. 2014; pp. U35-U43.
Murtuza, Bari, et al.; "Minimal Access Aortic Valve Replacements: Is It Worth It?"; Ann Thorac Surg, vol. 85, Issue 3; Mar. 2008; pp. 1121-1131.
Noad, Rebecca L., et al.; "A Pathway to Earlier Discharge Following TAVI: Assessment of Safety and Resource Utilization"; Catheterization and Cardiovascular Interventions, vol. 87, Issue 1; May 23, 2015; pp. 134-142.
O'Sullivan, Katie E., et al.; "Transaortic TAVI is a Valid Alternative to Transapical Approach"; J Card Surg, vol. 30, Issue 5; Mar. 10, 2015; pp. 381-390.
Permanyer, Eduard, et al.; "The 3f Enable Sutureless Bioprosthesis: Early Results, Safeguards, and Pitfalls"; J Thorac Cardiovasc Surg, vol. 149, No. 6; Oct. 15, 2014; pp. 1578-1583.
Phan, Kevin, et al.; "A Meta-Analysis of Minimally Invasive versus Conventional Sternotomy for Aortic Valve Replacement"; Ann Thorac Surg, vol. 98, Issue 4; Oct. 2014; pp. 1499-1511.
Rogers, Chris A., et al.; "An Open Randomized Controlled Trial of Median Sternotomy versus Anterolateral Left Thoracotomy on Morbidity and Health Care Resource Use in Patients Having Off-Pump Coronary Artery Bypass Surgery: The Sternotomy versus Thoracotomy (STET) Trial"; J Thorac Cardiovasc Surg, vol. 146, No. 2; Aug. 2013; pp. 306-316.
Roy, David A., et al.; "Transcatheter Aortic Valve Implantation for Pure Severe Native Aortic Valve Regurgitation"; J Am Coll Cardiol, vol. 61, No. 15; Feb. 20, 2013; pp. 1577-1584.
Schroeyers, Pascal, et al.; "Minimally Invasive Video-Assisted Mitral Valve Surgery: Our Lessons after a 4-Year Experience"; Ann Thorac Surg, vol. 72, Issue 3; Sep. 2001; pp. S1050-S1054.
Shrager, Joseph B., et al.; "Transcervical Thymectomy for Myasthenia Gravis Achieves Results Comparable to Thymectomy by Sternotomy"; Ann Thorac Surg, vol. 74, No. 2; Jan. 28, 2002; pp. 320-327.
Shrager, Joseph B., et al.; "Outcomes after 151 Extended Transcervical Thymectomies for Myasthenia Gravis"; Ann Thorac Surg, vol. 82, Issue 5; Nov. 2006; pp. 1863-1869.
Shrager, Joseph B.; "Extended Transcervical Thymectomy: The Ultimate Minimally Invasive Approach"; Ann Thorac Surg, vol. 89, No. 6; May 20, 2010; pp. S2128-S2134.
Thourani, Vinod H., et al.; "Use of Transaortic, Transapical, and Transcarotid Transcatheter Aortic Valve Replacement in Inoperable Patients"; Ann Thorac Surg, vol. 96, No. 4; Aug. 21, 2013; pp. 1349-1357.
Wong, Dennis T.L., et al.; "Relationship of Aortic Annular Eccentricity and Paravalvular Regurgitation Post Transcatheter Aortic Valve Implantation with CoreValve"; J Invasive Cardiol, vol. 25, No. 4; Apr. 2013; pp. 190-195.
Zannis, Konstantinos, et al.; "New Sutureless Aortic Valve Prosthesis: Another Tool in Less Invasive Aortic Valve Replacement"; Curr Opin Cardiol, vol. 27, Issue 2; Mar. 2012; pp. 125-129.
U.S. Appl. No. 15/148,749, Sutherland et al.

\* cited by examiner

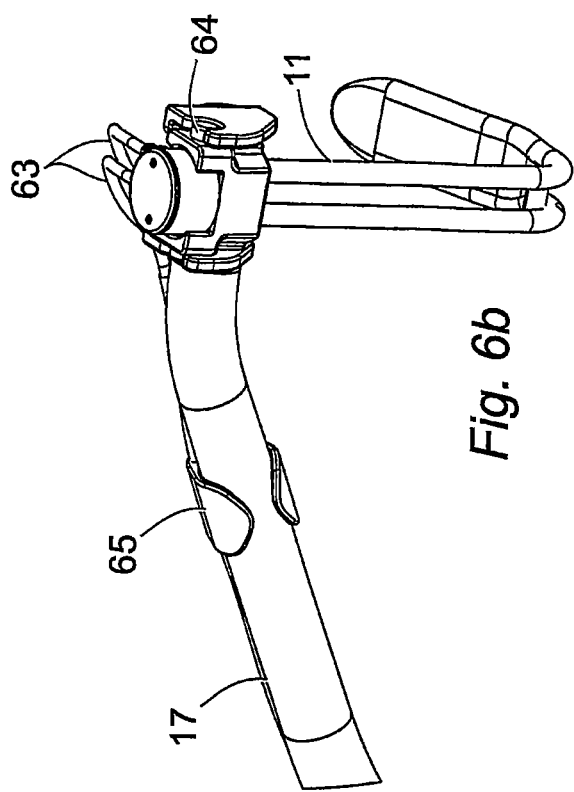
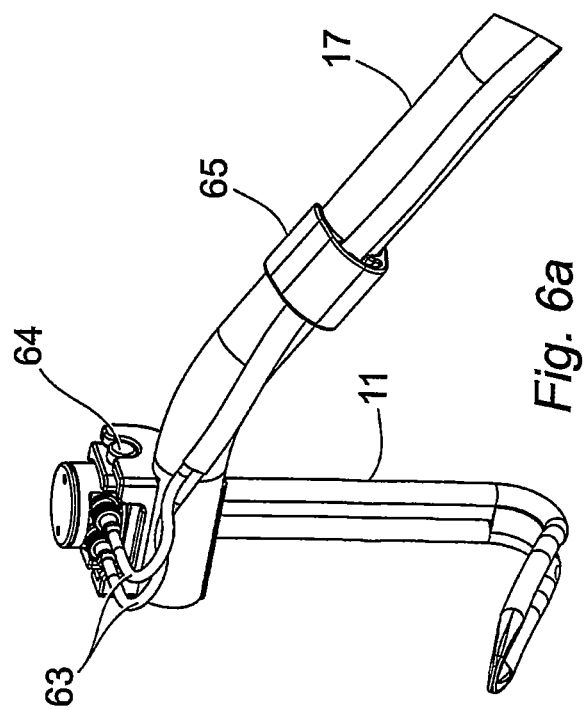

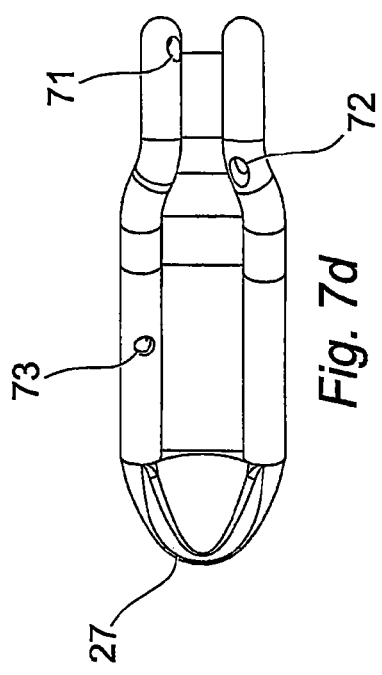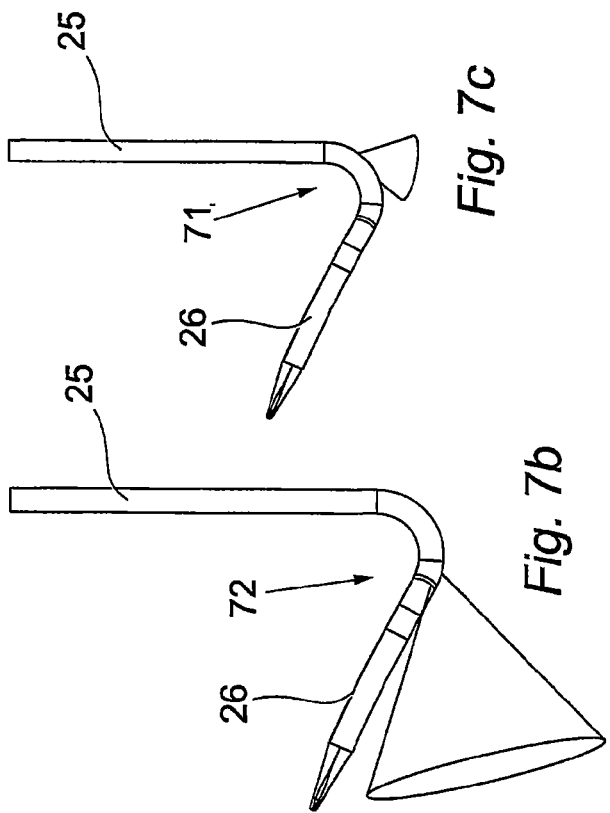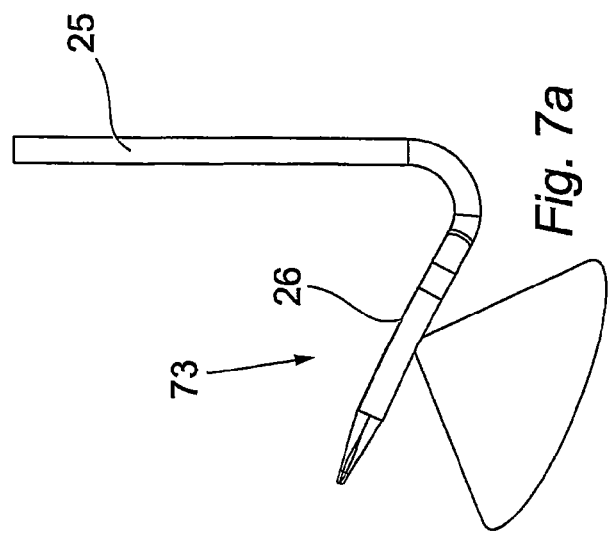

METHOD OF PERFORMING A MINIMALLY-INVASIVE INTERVENTION

CROSS-REFERENCE TO RELATED APPLICATIONS

This application is a continuation of, and incorporates by reference, for any purpose, the entire disclosure of U.S. patent application Ser. No. 12/863,091, filed Jan. 15, 2009.

FIELD OF THE INVENTION

The present invention relates to surgical instruments, especially to a method and device for facilitating minimally invasive cardiovascular or thoracic surgery. In particular, the invention relates to a device for expanding the thoracic basket to within its natural limits of expansion, directionally illuminating the chest cavity and providing surgical instrumentation to the surgical field.

BACKGROUND

In most incidences of thoracic surgery, including cardiovascular surgery, the operation necessitates the surgical division of the patient's sternum, such that the thoracic basket, or rib cage, can be prised apart. The division of the rib cage allows the surgeon access to the patient's thoracic cavity.

To effect the division of the sternum, generally, the patient's sternum is split by the use of a chest saw, and the two halves held apart using a retractor.

From the clavicle downwards, there are three main parts of the sternum—the manubrium, body and the xiphoid process. The three parts form the middle portion of the anterior wall of the thorax. The manubrium supports the clavicles, and the peripheries of the manubrium and body support the first seven pairs of ribs.

Conventional open-sternum surgery inflicts significant patient trauma and discomfort, requires extensive recuperation times, and may result in lifethreatening complications.

Incisions made over the chest are especially painful. The pain is unavoidable because movement exacerbates pain and the chest moves with respiration.

A significant amount of blood is typically lost from the raw surfaces of the two sides of the cut sternum. The need for blood transfusion is therefore relatively high.

Heat loss from wet surfaces is significant from open sternal wounds.

Chest incisions made through splitting the sternum only heal as fast as the fracture in the breastbone can heal. It typically takes several months for the bone to unite fully.

In some patients the fracture does not heal or becomes infected. This leads to long-term problems with stability of the chest cage or life threatening sepsis.

Furthermore, when the rib cage is divided using a conventional prior art sternal spreading retractor, more stress is placed on the shorter upper ribs than the longer lower ribs sometimes resulting in broken ribs.

Finally, the division of the chest can also lead to patients suffering from neurological disorders following open chest surgery, such as numbness in the hands.

To mitigate the damage that can be caused to the smaller upper ribs, which are connected to a neurologically important part of the plexus, surgeons have attempted to formulate more satisfactory ways of dividing the sternum and holding it thus.

One such idea has been to position the retractor in a lower position on the sternum to minimise damage to the weaker upper ribs. Such positioning has been found to result in less rib breakages, but the uneven pressure of the placement occasionally causes sternal fracture, leading to complications such as increased bleeding during surgery, and the need for repeated surgery to correct the sternal damage.

Accordingly, it would be desirable to provide minimally invasive chest cavity access through a neck incision, which has many potential benefits:
Less pain and trauma
Less bleeding
A smaller incision
Less heat loss during surgery
Reduced risk of infection
Decreased length of stay in hospital post procedure
Decreased recovery time Incisions made in the neck fall outside of the area of the body that moves with respiration so a wound here is inherently less painful. In addition it is easy to infiltrate the neck area with local anaesthetic. This can abolish pain altogether.

Less pain means less need for analgesia. The latter have side effects including sedation at higher doses. The reduced requirement for analgesia will enable patients to waken from anaesthesia more quickly and to breathe spontaneously.

Heat loss from wet surfaces is much less from a small neck incision than an extensive open sternal wound.

Blood loss will be minimal through a small neck incision in comparison to open sternal incisions. Because no bone is divided and bone marrow is not exposed.

Neck incisions heal more quickly than conventional openchest incisions. This is because they are smaller and the skin and soft tissues of the neck have a much better blood supply than those over the chest. The latter also reduces potential infections.

The present invention obviates or mitigates the foregoing deficiencies of the prior art devices and methods.

DISCLOSURE OF THE INVENTION

A retractor instrument for use in a surgical procedure comprises first and second components configured to provide a lifting means adapted to be inserted through an incision made in a part of the body, especially for the purposes of a minimally invasive procedure, said retractor being adapted to improve viewing of an internal part of the body by control of instrument dedicated illumination.

Thus according to a first aspect, an improved retractor blade incorporates a plurality of lights, which are independently controllable, and arranged to provide illumination to selected zones, e.g. to facilitate procedures within the surgical field. The light configuration may be selectively operated according to (a) a predetermined sequence programme, or (b) a sequence determined by a user of the retractor, in order to provide illumination at the most suitable place at any appropriate stage of the procedure.

Thus a retractor for use in a surgical procedure may comprise first and second components configured to provide a lifting means adapted to be inserted through an incision made in a part of the body for the purposes of a minimally invasive procedure, and further adapted to illuminate a surgical field within a body cavity within which a procedure is to be carried out, wherein the retractor comprises a blade portion incorporating a plurality of independent lighting devices configured to provide discrete illumination selectively to zones within the surgical field according to (a) a predetermined sequence programme, or (b) a sequence determined by a user of the retractor.

The retractor may be provided with switches, or connected to a microprocessor for controlling and actuating a pre-determined timed sequence of light operation.

Although it has been proposed in the past to adapt retractors to provide illumination, c.f. WO 2004/044632, there is to inventors' knowledge no device such as described herein that offers user-controlled illumination to discrete zones for particular stages of the procedure using independently controllable light sources.

Known illuminated retractors may generate glare through reflection of light from body tissues at some stage of the procedure e.g. during insertion of the instrument, and any such impediment to the vision of a surgeon as user of the instrument causes delay in the procedure and increases risk to the patient undergoing the procedure.

Known retractors equipped with lighting may be designed to deliver light only in one direction, whereas in fact it is desirable to view more than one anatomical structure during a procedure, and an instrument of the known type generally cannot appropriately achieve this objective.

In the present invention, suitable light sources include LEDs, and use of optical fibres in conjunction with an appropriate light source, the latter permitting any external light source to be adopted with use of suitable optics in the instrument to direct the light as required. Thus halogen or xenon light sources can be adopted. In some instances, such sources are preferable due to the ability to reduce and intensify the light output at will using known dimmer technology. Thus optical fibre bundles can be used to bring light directly into an intracorporeal operating field from suitably positioned light ports in the retractor.

LEDs offer known advantages as light sources, such as negligible heat output, small size and light weight, which enables them to be locally mounted upon the retractor and thereby directly within the intracorporeal operating field, and also offer directed light in a generally narrow beam spread. Thus these are efficient enough to selectively direct sufficient light using a portable power source, e.g. button cells, or batteries concealed within the instrument.

Avoidance of undue glare or stray light may be achieved by appropriate switching of lights, or use of anti-glare shielding in appropriate positions e.g. behind a light source from the point of view of a user.

Switching of the light sources can be manually controlled using switches upon the instrument, or controlled according to a predetermined timed sequence, e.g. using a microprocessor. Alternatively light output control is achievable by use of shuttering devices.

The direction and or breadth of light cast by the lighting devices may be controlled by use of prisms or lenses at the light ports.

Combinations of different lighting devices are contemplated to provide widespread lighting as in a floodlight, or localised lighting as in a spotlight, as may be required by the surgeon at a particular stage of the surgical procedure.

Optical components required for the lighting devices may be concealed or recessed within the retractor body parts, or may be mounted upon or project from the retractor body parts.

A retractor instrument contemplated for the purposes of this invention may be of generally hook or L-shaped configuration, wherein a first component is attachable to a hoist or lifting frame, and a second component which is generally referred to as a blade, projects therefrom to provide a surface adapted to contact a part of the body and move it in response to a lifting force being applied to said first component.

Such a retractor may comprise a first component configured for hand grip by a user so as to facilitate manipulation by a user, and a second component configured as a blade for insertion through an incision.

The first component, adapted as a hand grip, also can be usefully employed to house stored power units, controllers for light sources, optics components, etc.

The second component, configured as a blade part, can be usefully employed to carry a viewing device.

The viewing device can be in the nature of a telescope, a camera or an imaging device to transfer real time images to an external monitor.

Therefore according to another aspect of the invention, a retractor instrument may be configured to support and introduce imaging or viewing devices to the surgical field. Fibre optics are useful in this respect in conjunction with cameras, prisms, lens devices or telescopes.

Viewing devices such as charge coupled (CCD) and complementary metal-oxide-semiconductor (CMOS) devices are useful in camera technology and can be adopted in the invention.

In an embodiment, the blade is formed from a tubular frame and the space between a pair of opposed limbs of the frame can be utilised to house devices such as reusable camera modules. A cover plate over the frame provides strength to the blade to support weight and also to distribute loadings across the frame. The need to spread the load in the same way that a normal blade does arises from the fact that were only a frame structure to be introduced to the thoracic cavity, the limbs would contact costal cartilages on either side of the sternum. Costal cartilages are much weaker than bone, and at risk of breakage with resultant painful injury to the patient.

A push- or snap-fit clip may be used to attach such a camera module or the like device to the tubular elements of the blade.

The camera module may be mounted upon a ball or swivel housed within a two piece housing that defines a socket therebetween. The two piece housing may have front and rear portions formed to cooperate by an interference fit to form a socket mounting. The said portions are conveniently formed in plastics and fastened together by a staking technique, preferably by heat staking.

The portions may have shape-retaining flexible side elements including curved parts adapted to conform to a tubular frame element and serve as respective push-fit clamp elements allowing re-positioning along the tubular frame element at will. A ball member is disposed in the socket and depending upon the design of the housing portions, may be centred or offset.

Locking means to hold the ball in a predetermined position may be provided. Such locking means may be mechanical (e.g. a set or "grub" screw) or electromagnetic (e.g. a solenoid).

In this way a wide field of view is attainable and a camera such as a 30 degree camera with 70 degree field of view can be adopted in one embodiment of this invention.

The camera may be intended for intracorporeal use and is preferably removable for cleaning if it is of a reusable type, or for disposal if of the disposable type.

The camera may be integral with the retractor, and adapted for reuse as a whole unit, or the whole unit may be disposable.

Alternatively, the camera may be an extracorporeal camera to be used in conjunction with a telescope integrated with or adapted to fit within the retractor.

The retractor may comprise a first elongate component having at one end means for attachment or engagement with a lifting device and at the other end there is a second elongate component projecting therefrom at an angle in the range of 30 to 120 degrees, to facilitate lifting of a body part.

The components may be adjustably connected to permit a user to actuate and determine a suitable internal angle between the first elongate component and the second elongate component.

Thus according to one aspect of the present invention, a retractor for use in a surgical procedure comprises first and second components configured to provide a lifting means adapted to be inserted through an incision made in a part of the body for the purposes of a minimally invasive procedure, and further adapted to illuminate a body cavity within which a procedure is to be carried out, wherein the first and second components are adjustably connected to allow a user to selectively determine the angle between the first and second components.

A retractor instrument is of a generally hook or L-shaped configuration, which in accordance with an aspect of the invention, comprises a first component that is removably attachable to a novel lifting frame that includes an arm extending from an upstanding pivotal mounting whereby in use in association with an operating table, the arm may be moved from an overhanging position over the operating table to a position to one side of the operating table.

An advantage of this lifting frame design is that in the event that a complication arises during the surgical procedure, the retractor can be released and the frame can be quickly moved to facilitate access by operating theatre staff to allow emergency procedures or the like interventions to be conducted swiftly.

It will be understood that, although use of hoists in association with operating tables are not unknown in operating theatres, they normally comprise an operating table-fixed frame or "bridge-frame" consisting of a pair of opposed upright supports and a crossbar upon which lifting tackle is carried. The supports are normally clamped to the operating table, and require disassembly and removal by operating department assistants (ODAs) who have to be summoned to the operating theatre to remove the known type of bridge frame.

According to the invention, the use of a pivotal support arm, e.g. mounted upon a single upright support post offers numerous advantages in terms of ease of access, and saving of time which can prove critical to the well-being of a patient who develops complications during a surgical procedure. By allowing the retractor arm to be quickly swung away from above the patient, access by surgeons to perform an emergency intervention such as open-chest surgery is immediately available with no delay.

The support post may be ground-supported by insertion into a floor socket for the purpose, or into a weighted base unit, or preferably mounted upon one of the long edges of the operating table.

The support post provides a pivotal mounting for the overhanging support arm in one embodiment by provision of a free-running bearing within its assembled length, preferably a thrust bearing.

According to another aspect of the invention, the support post for the pivotally mounted lifting arm is attached by a frame that passes under the operating table and is fastened in a manner spreading the load across the underside of the operating table.

The fastening means for the under table frame may comprise quick-release clamps.

The under table frame may comprise a plurality of struts connecting between clamps for fastening the frame to the operating table. A three-point connection offers some advantages in use with respect to stability of the upright support post, and consequential fixing of the overhanging arm in a stable position over the operating table. Clamps may be adjustable on threaded members with engaging parts adapted to fit onto rails, or into channels provided on the longitudinal sides of the operating table, or optionally adapted to fit around or under longitudinal edges thereof.

An advantage of mounting the frame from underneath the operating table is that there is a clear unobstructed path for surgical instruments to be passed between an instrument table and the surgeon.

The support post may incorporate within its length a mechanical or electromechanical actuator such as a threaded rod movable within the support to serve as a "screw-jack" to elevate the arm without any discernible change in the angle of its overhang over the operating table.

This is desirable to avoid changing the orientation or position of the retractor or other instrument supported with the arm when inserted into a body part which could be harmful to the patient undergoing the surgical procedure.

The jack may be operated by means of a hand crank, or hydraulically, or by means of electromotive power. Preferably the jack incorporates a safety retention device to avoid slippage of the jack from a desired setting, i.e. to prevent the jack from lowering under load, especially to avoid dropback after lifting of a patient.

A mechanical system for converting rotational motion into linear motion may comprise a crank operatively associated with bevel gears mounted upon a rotatable shaft connected to or forming part of the screw jack, the gears being concealed within a shroud cover to prevent cross-contamination between gear lubricant and the external sterile field. Other gearing arrangements are possible e.g. worm gears.

It is currently contemplated that a hand crank with appropriate gearing may be preferred by some users due to the "hands-on" direct control perception derived from use of same. Minor adjustments may be achievable more easily with such a simple device in the hands of a skilled operator. Others may prefer to use a control system using electric motors or servo motors to smoothly elevate the arm by an appropriate amount within predetermined limits. In the case of an electric motor or hydraulic system, the controlling mechanism (a push button, say) can be kept within the sterile field.

In an embodiment the pivotally mounted arm has a free end adapted to receive a retractor or other surgical tool. The retractor or tool may be cradled in a suitably configured end part of the arm.

A retractor may be adapted to be suspended from the arm by provision of opposed pins adapted to seat in corresponding recesses in a cradle, whereby the retractor is free to pivot to allow forward and reverse motion for the blade of the retractor. Optionally the arm may incorporate a swivel mounting to support the retractor directly or the cradle from which it depends in order to allow additional freedom of movement laterally in respect of turning capability during manipulation of the retractor by a user.

Preferably the first and second components of the retractor are disposed at an angle of from 30 to 120 degrees.

Preferably the said angle is selected by the user to provide a user-actuated functional angle.

The retractor may be configured to be reversibly but securely coupled with the posterior of the sternum of a patient undergoing a surgical procedure.

The retractor may be configured to be reversibly but securely coupled with the interior face of the patient's sternum.

Preferably the retractor is configured to be reversibly but securely connected to pulling means in the nature of a hoist, crane or winch adapted to permit controlled lifting of a body part.

Preferably the retractor is configured to include channels through which instrumentation can be passed and affixed.

The retractor may be configured to introduce or provide tools or instruments for use in surgical manipulation.

The retractor may be adapted to draw or cut sutures.

Optionally the second component (blade) is configured to be inserted beneath the suprasternal notch of the sternum of a substantially supine patient.

Optionally the second component (blade) is configured to be inserted beneath the Xiphoid process of the sternum of a substantially supine patient.

Optionally the second component is configured to be inserted into the body of a substantially supine patient to facilitate access to the interior of said body by a surgeon.

Preferably the said second component (blade) is configured to reversibly but securely couple with the underside of the sternum manubrium of a substantially supine patient.

The first component may be configured to comprise a sprung clip at the distal end.

The retractor may be configured to confer a substantially vertical pulling force from a lifting device e.g. a winch, to a patient's sternum causing the patient's ribcage to expand optimally.

Preferably, the retractor is configured to confer a substantially vertical pulling force from the winch to patient's sternum causing the patient's rib cage to expand to its natural limits.

Preferably the retractor comprises surgical instrumentation for use in a procedure to be conducted within a body cavity.

Optionally the said surgical instrumentation includes means for use in suturing.

Optionally the said surgical instrumentation includes a means of grasping sutures.

Optionally the said surgical instrumentation includes a means of grasping tissue.

Preferably, the said surgical instrumentation is operable manually by the surgeon.

Alternatively, the said surgical instrumentation is operable manually by an assistant.

Optionally, the said surgical instrumentation is operable by an automated system.

Preferably the retractor is adapted to illuminate a body cavity by provision of at least two light sources, specifically, a first light source to provide widespread illumination to illuminate a body cavity within which a procedure is to be carried out, and at least one directed light source to permit a user to have a particular part within the cavity illuminated to facilitate the procedure.

Preferably the retractor comprises a fibre optic cable system connected to a low or substantially zero heat output light source, to illuminate the intended operative field within a body cavity, which is adapted to be inserted through a cannula to facilitate viewing of the operative field.

The low or substantially zero heat light source may be a halogen or xenon light source.

Optionally filters are employed with the light source to reduce the transmission of excessive heat to the operating site.

Preferably the low or substantially zero heat light produced is substantially the same or similar in electromagnetic spectrum to natural light.

Preferably the retractor comprises at least one telescopic lens connected to a video camera for observing the interior of a body cavity.

Preferably the said body cavity is the thoracic cavity, and the retractor is configured for insertion therein.

Optionally the retractor comprises an adaptor for receiving electrical power.

Optionally the retractor comprises a stored electrical power source.

Alternatively the retractor may comprise at least first and second components adjustably connected to include an angle of from 30° to 120°, and at least one of said components comprises a housing having an upper light occlusive part, and a lower light transmissive part, said housing incorporating internal mounting means for at least first light source, and external mounting means for a further light source, and the other component being adapted to be releasably attached to a lifting device.

Preferably the refractor includes a means to connect to an external power source when an alternative energy source is needed.

Said first and second sections may be permanently connected at a predetermined angle in respect of one another.

Optionally the angle at which said first section is connected to said second section is adjustable.

In an embodiment, a retractor comprises mutually spaced tubular elements paired to form an upstanding component of the retractor, wherein upper ends of the tubular elements engage with a cradle adapted for pendular mounting of the retractor upon an arm of a support frame, and at the end of the tubular elements remote from the cradle, curved tubular elements form a "heel" portion of the refractor, and further mutually spaced tubular elements extend laterally therefrom at an inclined angle to form the basis for a blade component of the retractor, and a cover plate overlies these inclined tubular elements to form a load distribution surface for contacting a body part, and a toe cap piece forms the tip of the blade component of the retractor, and wherein a first lighting device is positioned in a downwardly directed light port within a tubular part at the heel portion of the retractor, a second lighting device is positioned within a forwardly directed light port in ahead of the heel portion, and a third lighting device is positioned in a downwardly directed light port in a tubular part beneath the cover plate, each of said lighting devices being independently operable to provide discrete illumination selectively to zones within a body cavity according to (a) a predetermined sequence programme, or (b) a sequence determined by a user of the retractor.

One or more or the said lighting devices may be spotlights to provide localised lighting when required, and one or more may provide a wider beam of light in the manner of a floodlight to illuminate a larger field.

In embodiment, the first and second lighting devices are designed to serve as spotlights, and the third is designed to act as a floodlight.

The blade portion of the retractor may comprise spaced tubular parts and a viewing device may be mounted in a removable pod comprising a two-part plastics housing within which a ball mounting is captive, said housing having shape-retaining flexible wing elements for removably attaching the housing to the tubular parts by press-fitting between the spaced tubular parts, and the ball has a through-bore to allow insertion of the viewing device.

The viewing device may comprise an optical fibre bundle cable coupled to a camera or other image capture device whereby the viewed operating field can be transferred to an image display or storage device.

A minimally invasive procedure, such as chest surgery to replace a heart valve, comprises the steps of providing a retractor of the invention as discussed above (i) making an initial incision e.g. just above the sternal notch, sufficient to enable dissection of tissue for introduction of the blade of the retractor;

(ii) introducing the blade under the manubrium, and raising the retractor using a lifting mechanism to create a passage into the chest cavity;

(iii) operating a first light source that is located on the neck of the retractor and downwardly directed to facilitate mobilisation of tissues at the entrance to the wound and similar manoeuvres, (iv) switching off the first light source, and activating a second light source that is located on the underside of the blade of the retractor downwardly directed and configured to illuminate generally the pericardium, heart and great vessels;

(v) continuing surgical manoeuvres to accomplish the intended procedure, and including the step of operating a third light source that is located on the underside of the blade of the retractor forwardly directed and configured to direct light specifically onto a target tissue e.g. aortic valve.

BRIEF DESCRIPTION OF DRAWINGS

In the accompanying drawings:

FIG. 6a shows a front perspective view of the end of the lifting arm with a retractor seated in a cradle support;

FIG. 6b shows a rear perspective view of the end of the lifting arm with a retractor seated in a cradle support;

FIGS. 7a, 7b, and 7c show an embodiment of the light system with independently operable light sources positioned in light ports, and sequential illumination therefrom being represented by conical spread beam simulations;

FIG. 7d shows a view from underneath a modified retractor blade to illustrate an embodiment of the light system configuration;

MODES FOR CARRYING OUT THE INVENTION

Figure 1:
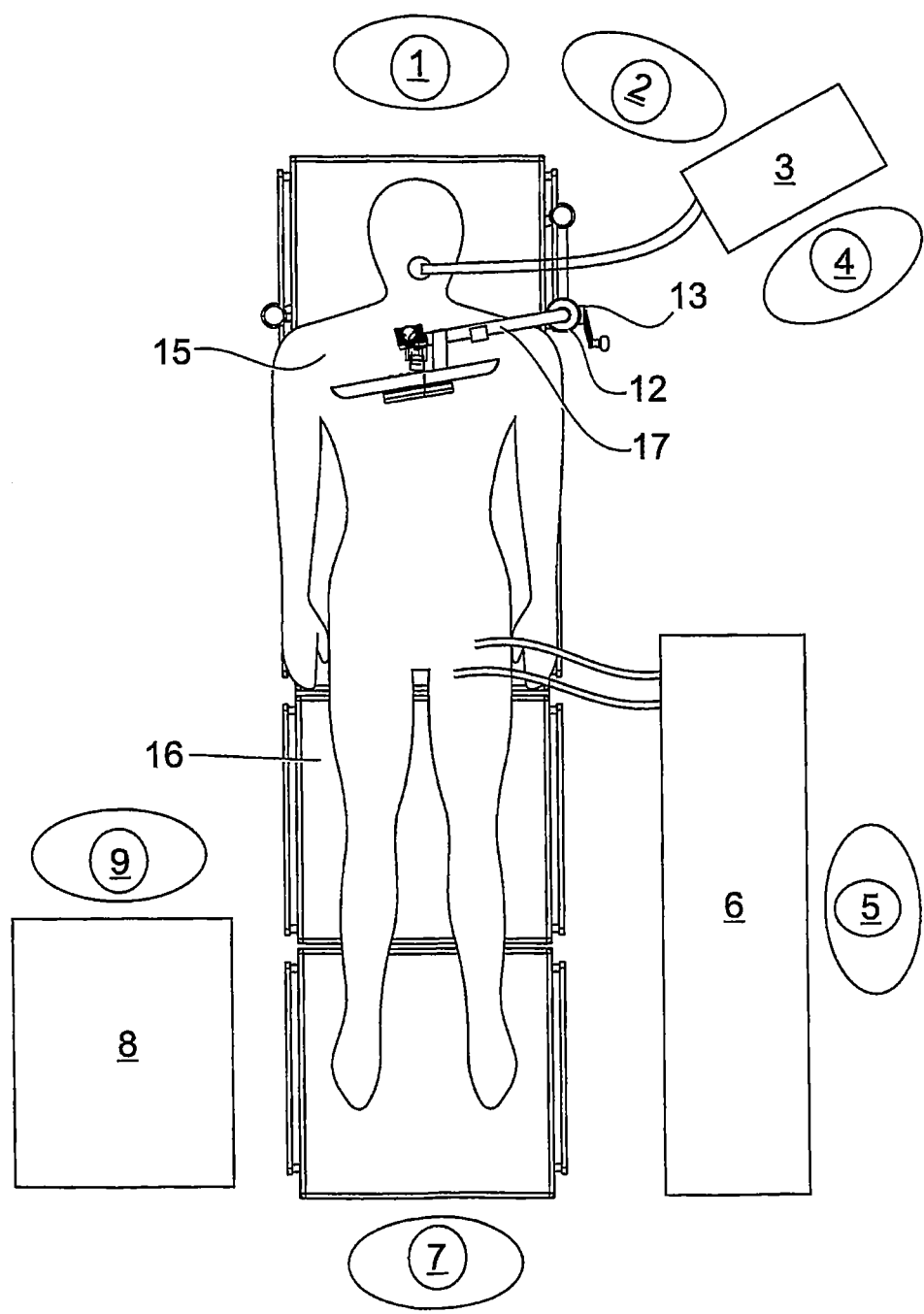
FIG. 1 is a schematic plan view of an operating table for receiving a subject undergoing a surgical procedure and a typical location of operating theatre staff and equipment.

The invention as referred to in its various aspects hereinbefore is intended for use in an operating theatre where space around an operating table is limited in view of the persons in attendance and the associated equipment required to support the patient. A plan view of an operating table 16 with floorspace "footprints" occupied by medical staff and apparatus is shown in FIG. 1.

Typically, the surgeon 1 who intends to conduct the operational procedure stands at head of the operating table 16 to provide best position for access to the patient for the purposes of an aortic valve replacement procedure.

The assistant surgeon 2 stands to the left of the surgeon 1. An anaesthetic machine 3 that is required to provide an accurate and continuous supply of medical gases (such as oxygen and nitrous oxide), mixed with an accurate concentration of anaesthetic vapour (such as isoflurane), for delivery to the patient at a safe pressure and flow is adjacent the head of the operating table, between the assistant surgeon 2 and the anaesthetist 4. Such a machine 3 may incorporate a ventilator, suction unit, and patient-monitoring devices. In the contemplated procedure described here for illustrative purposes, a perfusionist 5 operates a cardiopulmonary bypass machine 6 positioned to the side of the operating table 16. A circulating nurse 7 ("runner") at the outset is stationed at the foot of the operating table 16. The instrument table 8 is located to one side at the foot of the operating table 16, and attended by one or more scrub nurses 9.

Figure 2:
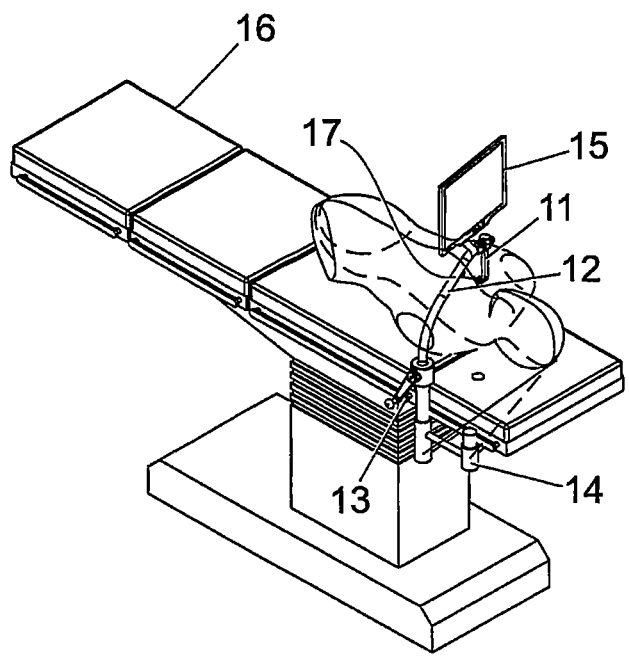
FIG. 2 is a partial perspective view of an operating table equipped with apparatus of this invention to facilitate the conduct of a surgical procedure upon a subject.
Figure 3:
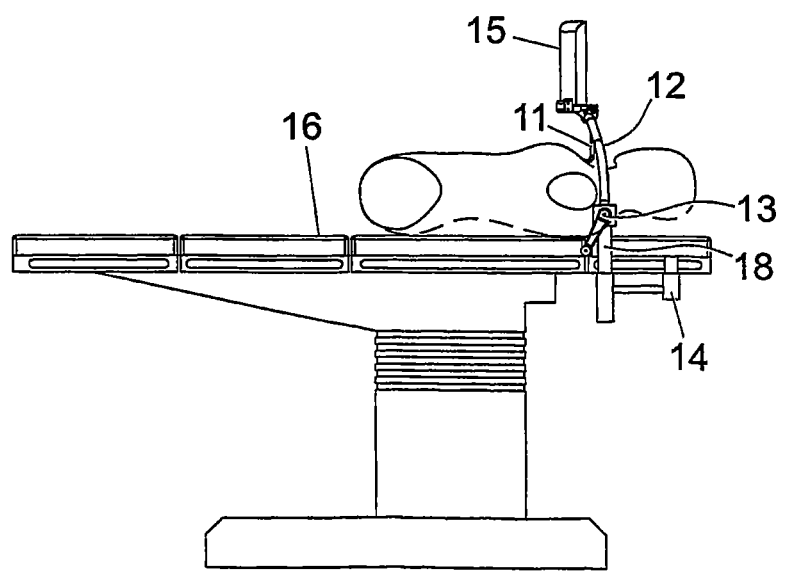
FIG. 3 is side view of the apparatus of FIG. 2.

In an embodiment of the invention as illustrated in FIGS. 2 and 3, a patient lies upon an operating table 16. Apparatus for supporting the surgical procedure includes a retractor 11 that is held above the patient by a lifting frame 12 with a pivotal arm 17 which overhangs the operating table 16 in an operational position, and that arm in turn is height-adjustably supported upon an upright support post 18 provided with a manually cranked winch 13. The support post is fixed to the operating table by means of a mounting frame 14 that is adapted to engage side rails on the operating table by clamps (not shown) that are adjustable upon threaded members to lock and secure the apparatus in position, but which allow its removal when required.

An advantage of having a pivotal support arm is that if a complication develops during the procedure, it is possible to quickly swing the support away from above the patient, enabling the surgeon to move to the right of the operating table and revert to an emergent open sternum approach.

The mounting frame 14 approximates to a right angled triangle when viewed in plan, and comprises a plurality of struts 52 (FIG. 5a), linking connecting posts 51 at apexes of the triangular configuration. These posts 51 may incorporate the adjustable clamps, and one of these posts also serves as the primary mounting for the support post 18 that conceals within it a lifting jack 54 forming part of the winch 13 that is operated by hand crank 55 through bevel gear system 56 upon thrust bearing 57. The bevel gear system 56 is concealed within a cover 53 to prevent cross-contamination between gear lubricant and the external sterile field.

A monitor 15 is also adjustably supported upon the arm 17 so as to be readily within the surgeon's field of view. This is especially advantageous to thereby allow the surgeon to view the procedure without shifting body position by turning to the side for example which would have the critical drawback of consequentially causing the loss of precise control of surgical instruments in the operating field.

The ability to adjust the position of the monitor with respect to the lifting frame enables it to be positioned optimally for comfort and performance of the surgeon. In an embodiment (not shown) a parallel linkage enables the monitor to be lowered in front of the retractor to allow the surgeon to look down upon the displayed image, which allows alignment of the visual with the motor axes of the operator. Use of such a parallel linkage allows the monitor to be moved (translated in a plane) without altering the viewing angle.

Figure 4:
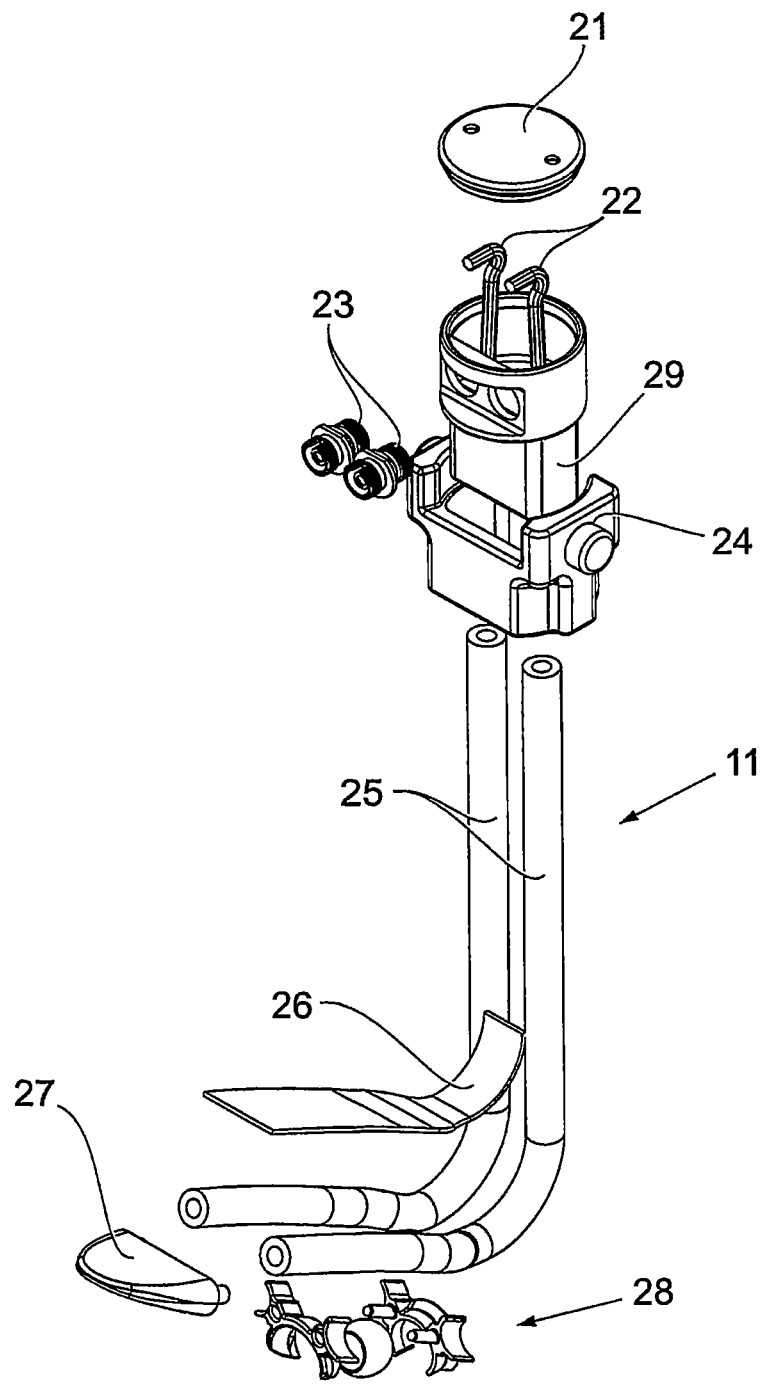
FIG. 4 is an exploded perspective view from above and to one side of a refractor assembly according to an embodiment of the invention.

The retractor 11 shown in FIGS. 2 and 3 depending from the arm 17 and inserted into an incision in the patient is shown in more detail in the exploded view of FIG. 4, and its attachment to the arm 17 is exemplified in FIGS. 6a and 6b.

Referring now to FIG. 4, the retractor 11 comprises mutually spaced tubular elements 25 paired to form an upstanding component of the retractor 11. The upper ends of the tubular elements engage with a cradle 24 forming the principle means of suspending the retractor from the end of arm 17.

Fibre optic bundles 22 are passed through the cradle 24 into the tubular elements 25, and light cable connectors 23 are operatively connected to the fibre optic bundles and located in housing 29 seated in the cradle 24.

At the lower end of the tubular elements 25, curved tubular elements form a "heel" portion of the retractor 11, and further mutually spaced tubular elements extend laterally therefrom at an inclined angle to form the basis for a blade component of the retractor. A cover plate 26 is applied over these inclined tubular elements to form a load distribution surface for contacting a body part. A "toe" cap piece 27 forms the leading edge of the blade component of the retractor 11.

Behind the toe cap piece 27 and underneath the cover plate 26 is a space between the tubular side elements that make up the blade component of the retractor 11.

That space is utilised to house a viewing or imaging device which in this embodiment is a camera mounted in a removable pod 28 shown in more detail in FIGS. 9a-9f. The removable pod consists of a plastics housing in two parts forming a front part 94 and a rear part 95 configured to define therebetween a socket within which a ball or swivel is captive when assembled. The two piece housing front and rear portions are formed to receive deformable pins 92 to lock them together e.g. by use of a heat staking method. The portions may have shape-retaining flexible wing elements 91 including curved parts adapted to conform with a tubular frame element and serve as respective push-fit clamp elements. A ball member 93 is captive in the socket such that it can pivot and swivel and has a central throughbore for receiving a viewing or imaging device, such as a camera or telescope.

Figure 8C:
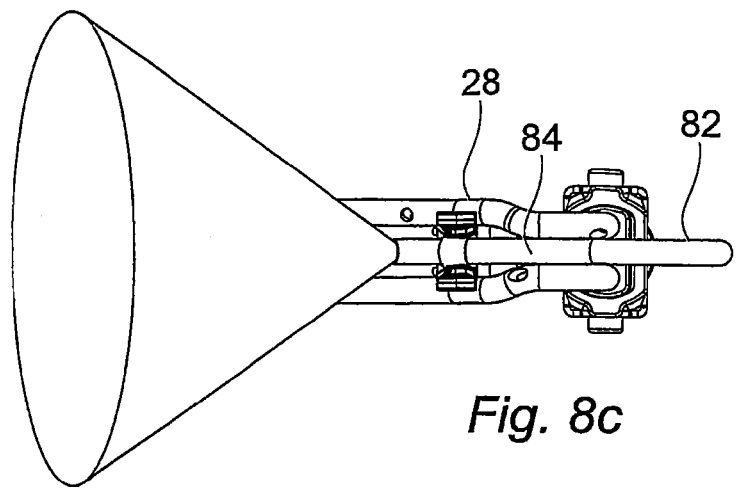
FIG. 8c shows a view from underneath a modified retractor blade to illustrate an embodiment of the viewing system configuration.
Figure 8A:
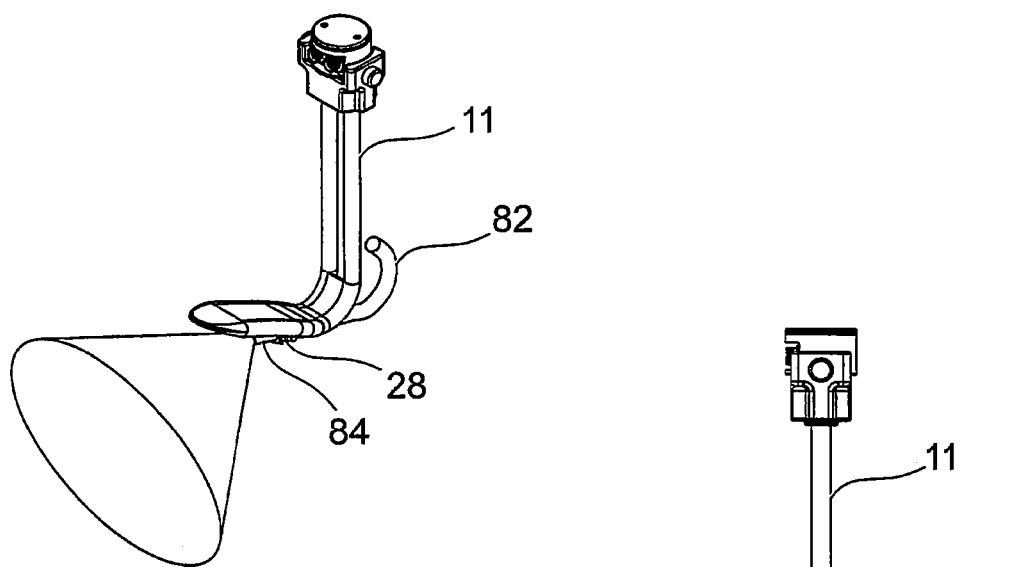
FIGS. 8a, and 8b show an embodiment of the viewing system equipped with a forwardly directed camera to be arranged to capture images of a surgical field in normal use, with the field of view schematically represented by conical spread beam simulations.
Figure 8B:
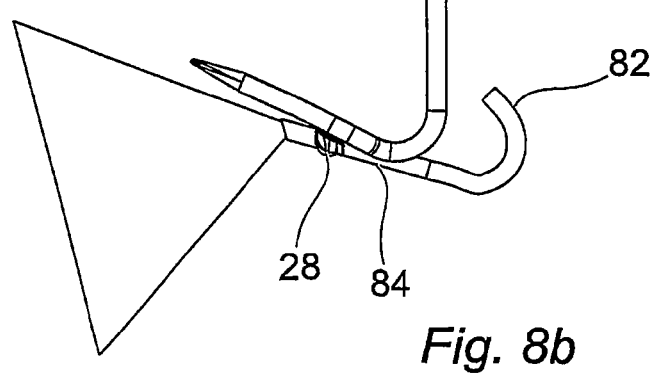
Figure 9A:
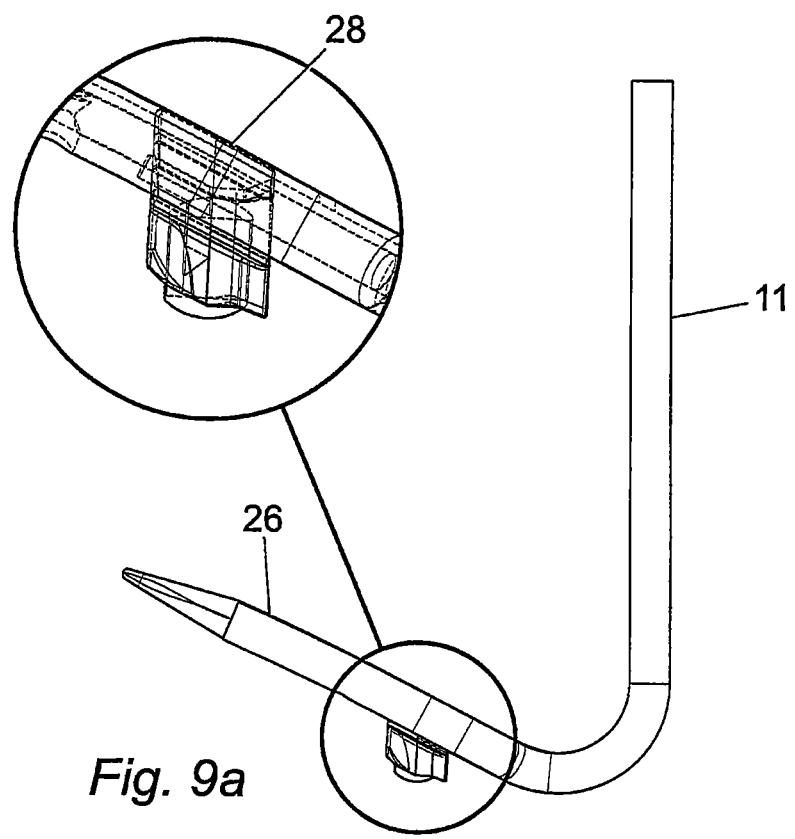
FIGS. 9a, 9b, show respectively a side view (FIG. 9a) of an embodiment of a retractor of this invention equipped here with a mounting device for receiving a camera mounted beneath the retractor blade, and an enlarged perspective view from above and to one side showing additional detail of the ball joint mounting (FIG. 9b)
Figure 9B:
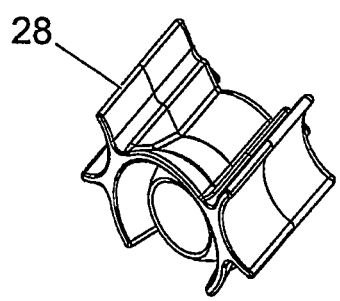
Figure 9E:
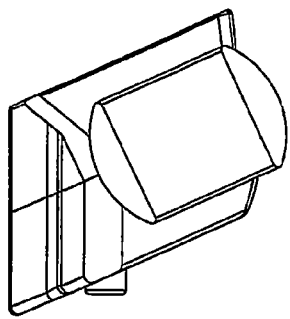
FIGS. 9c, 9d, 9e, and 9f, show respectively a side view of a mounting similar to that shown in FIG. 9b with detail of stake fastener pins, a perspective view from above and the front of such an assembled ball joint (FIG. 9d), and a central sectional view through the ball joint (FIG. 9e), a perspective view (FIG. 9f) from below and to one side of an assembled ball joint mounting.
Figure 9D:
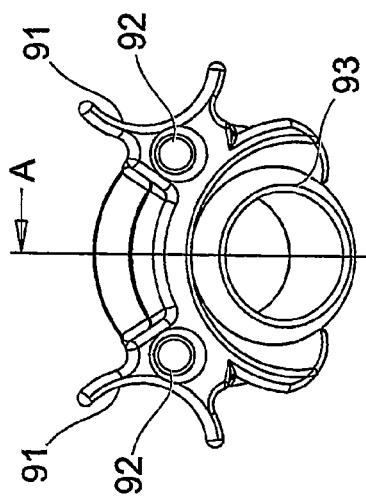
Figure 9F:
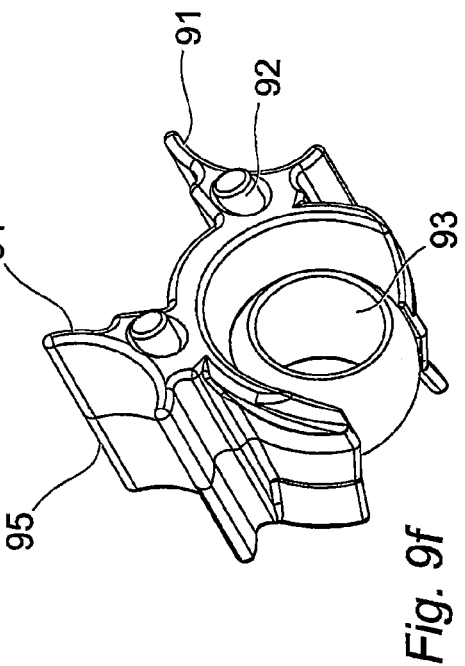
Figure 9C:
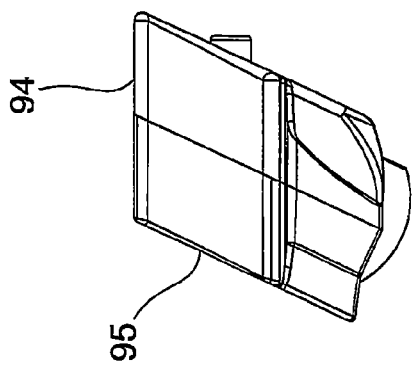

Referring to FIGS. 8a-8c, a camera 84 and camera cable 82 are fixed to the pod 28 with considerable freedom of movements under the retractor blade by virtue of the ball mount in the pod 28. The pod 28 is also slidable along the tubular elements making up the retractor blade. The cone representation in these figures illustrates the field of view available to the surgeon in use of the device.

Referring now to FIGS. 7a-7d, an embodiment of the unique lighting system is illustrated. Discretely controllable lighting is positioned within light ports 71, 72, and 73. The cone representations in FIGS. 7a-7c depict a field of illumination available selectively by appropriate switching means (not shown).

Figure 5A:
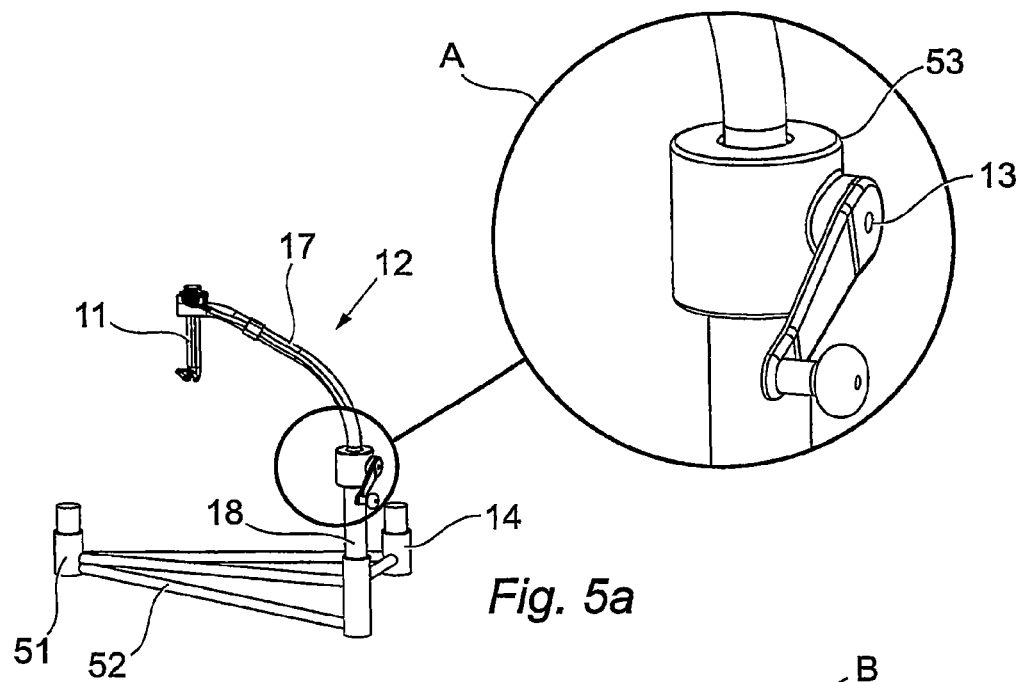
FIG. 5a is a perspective view of an embodiment of a lifting frame comprising a post and arm equipped with a retractor of this invention, with enlarged detail view "A"
Figure 5B:
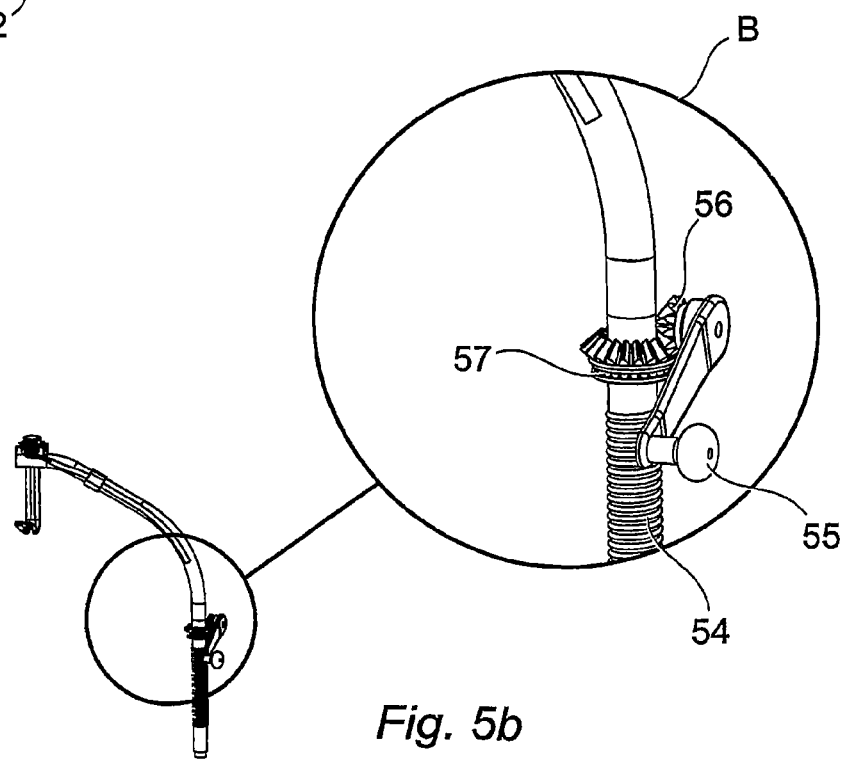
FIG. 5b is a perspective view of an embodiment of a lifting frame equipped with a retractor of this invention, as in FIG. 5a but with covers removed to reveal a lifting jack mechanism for elevating a lifting arm bearing the retractor, with enlarged detail view "B"

A retractor of this type is shown in an operative position depending from lifting frame 12 (depicted in isolation from the operating table) at the end of overhanging arm 17 in FIGS. 5a and 5b.

Further detail is shown in FIGS. 6a and 6b. Housing 29 is provided with pivot pins 64 that seat in corresponding recesses in the cradle 24.

Light cables 63 are connected to the connectors 23 and tidied against the arm 17 of lifting frame 12 by cable holder 65.

In a proposed use of such an embodiment of the invention, an operative procedure is outlined below:

Operative Procedure

A detailed description of the method of Trans cervical aortic valve replacement (AVR) procedure is listed below in note form and in a suitable sequence.

Aorta Exposure

Patient positioned with a bag or bolster under the shoulders and the neck extended Patient draped to expose the neck plus chest and groins Surgeon stands at the head of the table.

Skin crease incision made in the neck just above the sternal notch

Dissection of soft tissues and loose areolar tissue to create space behind the manubrium A retractor as illustrated in FIG. 4 is introduced into the wound, placed under manubrium and raised using the lifting mechanism of winch 13 to create a passage into the chest cavity Mobilisation of tissues at the entrance to the wound and dissection or mobilisation of the fatty remnants of the thymus gland just inside the wound is performed to improve access. These surgical manoeuvres are optimally achieved under illumination provided by a light located in a light port 71 at the heel of the retractor whose beam is directed in a generally downward direction with sufficient width of light beam to illuminate this anatomical area.

Once this dissection has been completed, the light at the heel of the retractor is turned off.

This minimises glare from light reflected off tissues located just inside the wound, which would otherwise prevent the surgeon from obtaining a clear view of structures further inside the chest.

A second light positioned in light port 73 designed to provide illumination of the pericardium, heart and great vessels is now turned on.

The pericardium is opened and the heart and great vessels (aorta and Main pulmonary artery) exposed. The aorta is mobilised and a tape passed around the vessel for control. This is optimally achieved with illumination provided by the second light.

Cardiopulmonary Bypass Established

Cardiopulmonary bypass (CPB) is next established via the femoral vessels.

The femoral artery and vein are exposed using skin crease incision in the groin.

Heparin is administered and the femoral artery and vein cannulated under trans-oesophageal echo (TOE) imaging. Cardiopulmonary bypass is commenced.

Aortic Valve Replacement Performed

A cross clamp is placed across the aorta using a long trans thoracic clamp placed through the right chest, via the 2nd intercostal space in the mid-clavicular line.

Cardioplegia instilled into the aortic root and the heart arrested

During this time the left ventricular cavity is monitored by TOE for evidence of distension.

The aorta is opened around half of circumference under illumination provided by the second light.

The third light positioned in light port 72 is now turned on. This light is designed to shine inside the open aorta to illuminate the aortic valve. The second light positioned in light port 73 may optionally be turned off or left on.

The surgeon's view of the aortic valve is enhanced by a camera 84 located on the retractor. This camera provides the surgeon with a magnified view of the inside of the aorta and aortic valve area. Furthermore, it allows the surgeon to adopt a more comfortable viewing position so that surgery can be performed more easily The camera is attached to the under surface of the retractor. Therefore, it is tucked away under the sternum and out of the direct line of sight of the surgeon through the wound and out of the path of surgical instruments also introduced through the wound.

A 0 degree-90 degree camera mounting allows the camera to be angled even further out of the path of instruments. A 30 degree camera is typically used.

The camera position can be adjusted axially (in/out), or by roll (rotation), yaw (side to side) and pitch (up and down) for optimal viewing.

The following parts of the procedure are optimally performed by the surgeon using the camera and viewing on a screen or screens in the operating theatre.

The image can be relayed to any screen in the operating theatre for scrub staff, anaesthetist, perfusionist and surgical assistants to see. However, a screen located immediately above the wound, within the sterile field and adjustable in its position is best for the surgeon.

The native aortic valve is excised using minimally invasive surgical instruments.

The valve orifice is sized using conventional valve sizers and a suitable prosthetic valve selected.

The prosthetic valve is implanted using interrupted or continuous sutures, according to surgeon preference.

Aortomy closed in conventional manner

Pacing wire attached to the epicardium of the right ventricle

Air excluded from the heart under TOE control

Vent placed back into aortic root to aspirate air

Cross clamp removed

Patient weaned from CPB, decannulated and protamine administered

Groin wound closed in layers

Redivac drain brought out through the neck adjacent to the incision or through the lower chest under observation of the camera Pacing wire brought out through the neck adjacent to the incision or once again through the lower chest under observation of the camera The camera and retractor are withdrawn from the chest cavity.

Wound closed in layers

In another embodiment of the present invention not shown, the retractor is configured to comprise a telescope connected to a video camera for observing the interior of the patient's thoracic cavity. Said telescope may be positioned by the surgeon, and the video camera is able to project pictures to a screen in the operating theatre. The surgeon is able to observe and magnify the area of interest within the patient's thoracic cavity.

In a variant of the previous embodiment, the telescopic video camera is equipped with a low or non-heat light source, such as an LED. The light is directed together with the video camera to illuminate the area observed by the video camera. The telescopic camera is configured to be manually aimed by the user in an appropriate direction.

In a yet further embodiment, the telescopic video camera and lighting of the previous embodiment is configured to be directed or guided by the user in an appropriate direction using a signal from a remote control module. The means of communicating a signal between said remote control module and said telescopic camera is a means of wireless communication, such as radio frequency (RF) communication, microwave communication, or infrared (IR) short-range communication. Suitable radio control systems include pulse width modulation (PWM), pulse position modulation (PPM) and spread spectrum technology, which will actuate the various control surfaces within the structure of the retractor and telescopic camera using servomechanisms. The RF device includes a microchip comprising an integrated circuit for storing and processing information, modulating and demodulating a (RF) signal, and an antenna. Power for the device is both from a stored charge device such as a button cell, coin cell or battery, and mains electricity.

In an alternative embodiment, a videoscopic camera that is positioned on the sternal portion of the retractor is controllable by voice activated positioning.

In a still further alternative embodiment, a videoscopic camera which is positioned on the sternal portion of the retractor is controllable by a system comprising a sensor placed on the surgeon's head configured to track the surgeon's head positioning.

In yet another alternative embodiment, the telescopic camera and lighting of the previous embodiment is guided by a hard wired remote control mechanism.

In a further variant, a fibre optic is utilised in lieu of or together with the adjustable light source of the previous embodiment. The fibre optic is able to relay the image of the interior of the patient's thoracic cavity to a camera outside of the cavity. The images are then fed through a conventional digital image processor and relayed onto monitors in the theatre.

It should be noted that all devices and equipment described above and used to comprise or used with the present invention would be made from materials that may be coated in or comprised of material which can be sterilised to meet the accepted hygiene standards of modern surgery.

It should be further noted that various adjustments and reconfigurations are possible to the illustrated embodiment as described above within the scope of the invention as will be apparent to those skilled in the art.

The invention claimed is:

1. A method comprising:
applying a lifting force to a retractor inserted into an incision that is formed superior to a sternal notch of a patient, the retractor extending under a manubrium of the patient, the lifting has been changed to force opening the incision, the retractor having a blade portion, a neck portion upstanding from the blade portion, and a curved heel portion formed between the blade portion and the neck portion;
selectively illuminating, via a first light port disposed on an outer surface of the curved heel portion of the retractor, fatty remnants of a thymus gland for mobilization or dissection to improve access to a pericardium;
selectively illuminating, via a second light port disposed on an underside of the blade portion of the retractor, at least one of the pericardium, a heart, an aorta, and a pulmonary artery, such that the first light port and the second light port are independently operable; and
exposing the aorta.

2. The method of claim 1, comprising establishing a cardiopulmonary bypass.

3. The method of claim 2, comprising:
clamping the aorta;
arresting the heart;
opening the aorta; and
illuminating an interior of the aorta and an aortic valve.

4. The method of claim 3, comprising viewing, via a camera, a magnified view of the interior of the aorta and the aortic valve.

5. The method of claim 4, wherein the viewing comprises utilizing a screen disposed above the incision.

6. The method of claim 4, comprising adjusting the magnified view by adjusting at least one of an axial position, a roll position, a yaw position, and a pitch position of the camera.

7. The method of claim 1, comprising replacing an aortic valve.

8. The method of claim 1, comprising:
illuminating an interior of the aorta and an aortic valve comprises utilizing light emitted from a third light port of the retractor.

9. The method of claim 1, comprising turning off the first light port thereby reducing reflected light near an entrance to the incision.

10. The method of claim 1, wherein the applying the lifting force comprises utilizing a winch that is operatively coupled to the retractor.

11. The method of claim 1, comprising opening the pericardium to expose at least one of the heart, the aorta, and the pulmonary artery.

12. A method comprising:
responsive to a lifting force, a retractor opening an incision formed superior to a sternal notch of a patient, the retractor having a blade portion, a neck portion upstanding from the blade portion, and a curved heel portion formed between the blade portion and the neck portion;
selectively illuminating, via a first light port disposed on an outer surface of the curved heel portion of the retractor, fatty remnants of a thymus gland for mobilization or dissection to improve access to a pericardium; and
selectively illuminating, via a second light port disposed on an underside of the blade portion of the retractor, at least one of the pericardium, a heart, an aorta, and a pulmonary artery such that the first light port and the second light port are independently operable.

13. The method of claim 12, comprising:
facilitating opening of the aorta; and
illuminating, via the retractor, an interior of the aorta and an aortic valve.

14. The method of claim 13, comprising providing, via a camera, a magnified view of at least one of the interior of the aorta and the aortic valve.

15. The method of claim 14, wherein adjustments made to at least one of an axial position, a roll position, a yaw position, and a pitch position of the camera adjust the magnified view.

16. The method of claim 14, wherein the camera is disposed on the retractor.

17. The method of claim 12, comprising facilitating replacement of an aortic valve.

18. The method of claim 12, wherein the lifting force is applied via a winch operatively coupled to the retractor.

19. A method comprising:
responsive to a lifting force, a retractor opening an incision formed superior to a sternal notch of a patient, the retractor having a blade portion, a neck portion upstanding from the blade portion, and a curved heel portion formed between the blade portion and the neck portion;
selectively illuminating, via a first light port disposed on an outer curved surface of the heel portion of the retractor, an entrance to the incision;
selectively illuminating, via a second light port disposed on an underside of the blade portion of the retractor, at least one of a pericardium, a heart, an aorta, and a pulmonary artery;
selectively illuminating, via a third light port disposed on the retractor, an interior of the aorta and an aortic valve; and
facilitating replacement of the aortic valve.

20. The method of claim 19, comprising providing, via a camera, a magnified view of at least one of the interior of the aorta and the aortic valve.

21. The method of claim 20, wherein adjustments made to at least one of an axial position, a roll position, a yaw position, and a pitch position of the camera adjust the magnified view.

22. The method of claim 19, wherein the lifting force is applied via a winch operatively coupled to the retractor.

* * * * *